(12) United States Patent
Mackool

(10) Patent No.: US 10,105,044 B2
(45) Date of Patent: Oct. 23, 2018

(54) ENDO-OPTIC ILLUMINATOR

(71) Applicant: Richard Jonathan Mackool, Astoria, NY (US)

(72) Inventor: Richard Jonathan Mackool, Astoria, NY (US)

( * ) Notice: Subject to any disclaimer, the term of this patent is extended or adjusted under 35 U.S.C. 154(b) by 0 days.

(21) Appl. No.: 15/429,964

(22) Filed: Feb. 10, 2017

(65) Prior Publication Data
US 2017/0231483 A1 Aug. 17, 2017

Related U.S. Application Data

(60) Provisional application No. 62/294,803, filed on Feb. 12, 2016.

(51) Int. Cl.
*A61B 3/10* (2006.01)
*A61B 3/00* (2006.01)
*A61B 3/13* (2006.01)
*G02B 23/24* (2006.01)

(52) U.S. Cl.
CPC .......... *A61B 3/0008* (2013.01); *A61B 3/0075* (2013.01); *A61B 3/13* (2013.01); *G02B 23/2469* (2013.01)

(58) Field of Classification Search
CPC ........... A61B 3/14; A61B 3/12; A61B 3/0008; A61F 9/008
USPC .................................................. 351/200-246
See application file for complete search history.

(56) References Cited

U.S. PATENT DOCUMENTS

| | | | |
|---|---|---|---|
| 8,348,430 B2* | 1/2013 | Artsyukhovich .... | A61B 3/0008 351/221 |
| 2003/0088257 A1* | 5/2003 | Awh ........................ | A61F 9/007 606/161 |
| 2011/0028790 A1* | 2/2011 | Farr .................... | A61B 1/00052 600/187 |
| 2015/0282749 A1* | 10/2015 | Zand .................... | A61B 5/0071 600/301 |

* cited by examiner

*Primary Examiner* — Mohammed Hasan
(74) *Attorney, Agent, or Firm* — Charles McCloskey

(57) ABSTRACT

An endo-optic illuminator has a compartment, a divider within the compartment, and a fiber optic cable in optical communication with the divider and with the light source of a microscope. The fiber optic cable transmits the light through its length. The cable has two ends: a tip and a base. A user then positions the cable to emit light with the tip proximate a patient's eye. Opposite the tip, the base connects the cable to the light source. The divider redirects light from the light source into the base of the fiber optic cable and then onward to illuminate its tip. The divider includes a prism, beam splitter, mirror flip, occluder, shutter, and the like. The fiber optic cable transmits light with less than a 10% loss of candlepower along its length. The illuminator replaces a second separate light source currently used by ophthalmologists.

12 Claims, 3 Drawing Sheets

ENDO-OPTIC ILLUMINATOR

CROSS-REFERENCE TO RELATED APPLICATION

This non-provisional application claims priority to provisional application No. 62/294,803 filed on Feb. 12, 2016 all of which are owned by the same inventor.

BACKGROUND OF THE INVENTION

The endo-optic illuminator generally relates to microscopy equipment and more specifically to a light transmission cable and related hardware.

Developed over the millennia, people have eyes to see. An eye has various tissues that receive and focus light upon a retina that converts the light into electrical signals transmitted to a person's brain for interpretation. In the vicinity of a person, light encounters a cornea as the first part of the eye. The cornea, generally transparent, admits light further into the eye. The cornea has its own constituent parts where the endothelium is the extremely thin, innermost layer of the cornea. Inwardly from the cornea, an eye has its lens of flexible tissue.

Various fine muscles attach to the lens and stretch the lens to adjust its focus as desired by the person seeing an object at a certain distance. The soft lens seeks to modify the focal power of the lens within an eye. The eye lens, inwardly from the cornea, provides the focusing for images. The eye lens comes from concentric protein layers that move well during the youth of a person but then gradually thicken and lose pliability over the years. Reaching the age of forty years, many people then encounter difficulty in focusing because of this eye lens thickening, or presbyopia. Then later in a person's life, the lens may become opaque, creating a condition known as a cataract.

Whether young or old, a person's eye may only see so much. To see smaller things than with the naked eye, optical microscopes were developed in the last few centuries. The optical microscopes utilized lenses with various refractive powers, various numbers of those lenses, concave and convex characteristics of the lenses, combinations of the lenses, and the like to enlarge what was once too small to see. In doing so, the optical microscopes sacrifice depth of field for fine detail of small objects. Optical microscopes utilize light of wavelengths primarily in the visible spectrum.

In recent years, various physicians and microscope manufacturers have sought close views of the structures of a human eye. Manufacturers have developed microscopes and related stands suitable for ophthalmic and optometric uses in an office setting. Those microscopes have a position and orientation near a patient's eye upon placement of a patient's head in a stand near the microscope.

DESCRIPTION OF THE PRIOR ART

As part of diagnosis and treatment of various ophthalmic conditions, a surgeon, other medical provider, or user, seeks a close view of a patient's eye. The user may operate a headlamp with a low power lens that rotates down in front of the user's own eye. This headlamp and lens allows for seeing the exterior of the patient's eye, the eye socket, and related anatomical structures. A user may also employ an optical microscope typically without a base.

The user places the microscope near the patient's eye but at the focal point of the microscope. Depending on the magnification used, the user may have to move the microscope outwardly or inwardly relative to the eye for a focused image to appear to the user. On rare occasions, a user has placed the microscope directly upon the patient's eye, particularly the cornea.

Various light sources have also appeared for ophthalmic uses in clinical settings of wide description.

The publication to Gil, No. 2007/0159600 shows a transcleral ophthalmic illumination system. This system has a light source, fiber optic cable, and focusing optics. The focusing optics utilizes rotary wheels as at 7, 12 for shaping, sizing, and coloring the illuminated spot. This system also has computerized controls as shown in FIG. 4 and described in para. 47. This system may use light from an existing instrument or may use its own light.

The patent to Svetliza, U.S. Pat. No. 6,267,752, describes a multi-function eyelid speculum. This speculum has a main body with hollow rings for aspiration and irrigation to an eye. The speculum also describes an embodiment for illuminating the sclera. We call your attention to FIGS. 4, 5, 6, 8a, 8b. Those figures show the illuminating construction for the speculum, particularly FIGS. 8a, 8b. This speculum has direct contact upon an eye, c. 5 I. 47, and has light elements in their own ring within the speculum.

The patent to Mastel, U.S. Pat. No. 5,312,393, shows a ring lighting system for microsurgery. This system places lighting directly upon a microscope housing and directs the light into the microscope optics.

The patent to Kleinberg, U.S. Pat. No. 5,155,509, has an oblique illumination device for a microscope. This device attaches optical devices to a microscope, such as beam splitters.

Lyons' patent, U.S. Pat. No. 5,054,906 illustrates an illuminating speculum. This speculum has two tubes upon two arms of the speculum. The tubes carry fiber optic cable powered by an external light source.

U.S. Pat. No. 4,565,197 to Daly describes a laser ophthalmic surgery guidance system. The system overlays images from an aiming beam so that clear images visible by the surgeon indicate the targeted area for surgery.

The patent to Martinez, U.S. Pat. No. 3,944,342, has a photographic apparatus for a slit lamp. FIG. 8 shows a light sensor with a photoelectric cell in electrical communication to a camera. The light sensor cooperates with the shutter speed and aperture of the camera.

And the patent to Laforcade, U.S. Pat. No. 3,930,504 shows a light coagulator. This coagulator has a parallel beam source, a first lens, an adjustable aperture diaphragm, a second lens, and a rotatable mirror. The light source has a further description of a lamp with a symmetric concave reflector. This patent shows a device that provides light separately from other instruments.

The present invention overcomes the disadvantages of the prior art and provides an endo-optic illuminator that allows a user to deliver light upon an eye beneath a microscope. The present invention allows a user to illuminate an eye with one less piece of equipment and to treat the eye simultaneously.

SUMMARY OF THE INVENTION

Generally, the endo-optic illuminator attaches to an existing microscope upon a stand, either table placed or pole placed. The microscope has its light source illuminating a target area beneath the lens and generally opposite an eyepiece. The illuminator taps into the light generator component of a microscope. The present invention has a compartment, a divider within the compartment, and a fiber optic cable in optical communication with the divider and which taps into the light source of a microscope. The fiber optic cable then transmits the light through its length. A user then positions the cable and this light source as desired proximate an eye. The divider redirects some or all light from the light source into the fiber optic cable and then onward to illuminate its tip as this light source. The divider includes a prism, beam splitter, mirror flip, occluder, shutter, and the like. The fiber optic cable transmits light with less than a 10% loss of candlepower along its length. The illuminator replaces a second separate light source currently used by ophthalmologists.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide an endo-optic illuminator that allows a user to have one light source proximate an eye during an ophthalmic procedure.

Another object is to provide such an endo-optic illuminator that co-locates an illumination device proximate the viewing location of a microscope.

Another object is to provide such an endo-optic illuminator that loses less than a 10% of candlepower along its length.

Another object is to provide such an endo-optic illuminator that avoids anastamosis by a surgeon or equipment operator between cables of the invention and related to the invention.

Another object is to provide such an endo-optic illuminator that has a reasonable cost of manufacturing so that ophthalmologists, clinics, hospitals, and organizations can readily purchase the digital microscope through catalogs, suppliers, vendors, and supply sources.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
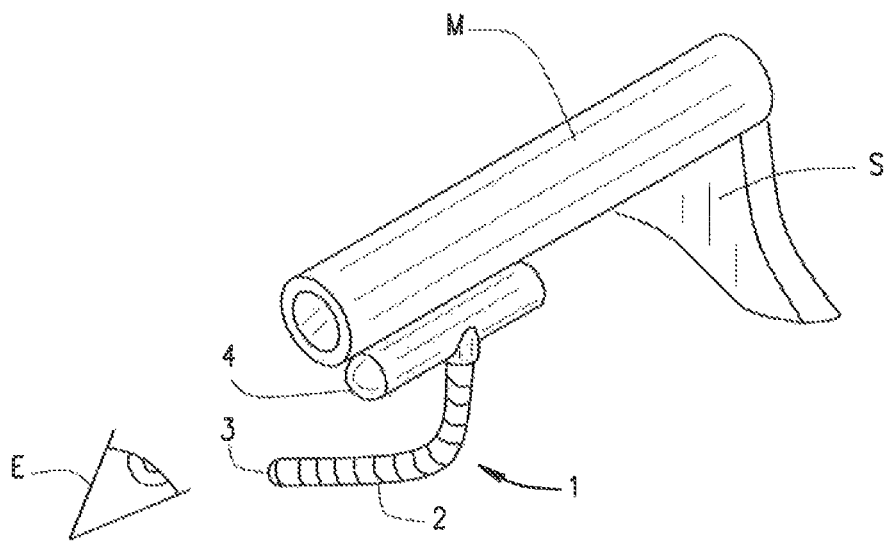
FIG. 1 shows a perspective view of the invention upon an existing microscope.

The present art overcomes the prior art limitations by providing an endo-optic illuminator that collocates upon a microscope with related diagnostic and treatment devices. Though this description refers to light, the Applicant foresees the invention as generating and transmitting other forms of radiation, including infrared, ultraviolet, gamma, and radio. Thus, the references to light that follow also include other radiation. FIG. 1 shows the invention 1 of the endo-optic illuminator upon an along a microscope M extending outwardly from a stand S as shown. The microscope housing, towards its working end, supports a light generator, or radiation generator, with an open end 4 co-located with the working end of the microscope. A fiber optic cable 2 of the invention 1 connects to the light generator inwardly from the open end 4. The cable 2 has partial inherent rigidity which allows a user to direct a tip 3 for emitting light from the cable to a target object, such as an eye undergoing surgery. The cable has a length suitable for spanning the typical gap from a microscope to a patient's target area with some additional length to allow for curvature of the cable and offset from the microscope as needed by the user.

Figure 2:
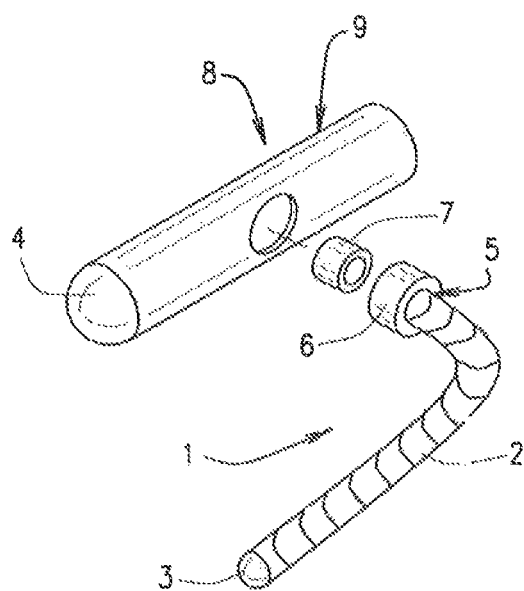
FIG. 2 describes an exploded view of the invention.

FIG. 2 then shows an exploded view of the invention 1 removed from the microscope of FIG. 1. The invention has its fiber optic cable 2 of a slender, flexible, elongated shape with a diameter. The cable also serves as a member cable of transmitting radiation, including light. The cable, or member, has a length at least five times that of the diameter, and has two ends. The cable has its tip 3 upon one end from which emits light carried through the length of the cable. Opposite the tip, the cable 2 has a base 5 upon the opposite end to which connects a fitting 6. The base 5 may also have a socket like shape. The fitting has a generally round shape and is preferably female for connection to the light generator as previously shown in FIG. 1. Inwardly from the fitting, the invention 1 has its divider 7 which directs light into the cable 2 or alternatively through the light generator to its open end 4. A user operatively moves the divider between an open position and a close position to direct light to the cable 2 or to the open end 4 at the working end of the microscope M. Inwardly from the divider, the light generator as at 8 has a case 9 here shown has a slender cylinder, though other shapes are foreseen. The case has two opposite ends with the open end 4 shown and capable of emitting light from it. The case includes a compartment 10 that admits the divider 7 into the light generator so that the divider may intercept and direct light to the cable 2 or alternately to the open end 4.

Figure 3:
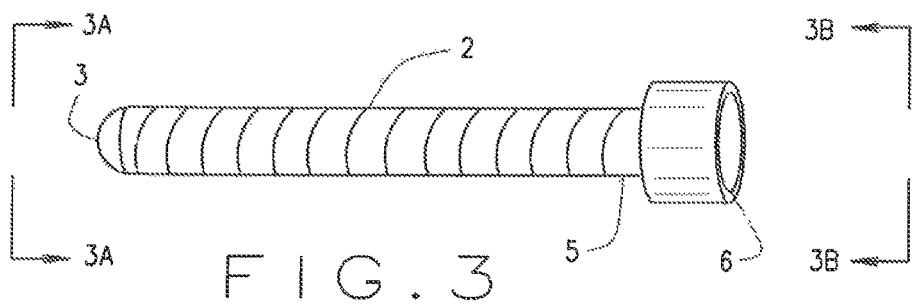
FIG. 3 provides a side view of the cable of the invention.

The fiber optic cable 2 has its elongated, slender form shown in FIG. 3. The cable transmits light and other radiation through its length from the fitting 6 to the tip 3 at the opposite end. The cable has its inherent construction that transmits the light through its length using internal reflection with limited loss of optical signal strength, that is, less than a 10% loss of candle power. The cable has a sheath of an opaque material with rugged construction to withstand user manipulation and a surgical environment. In an alternate embodiment, the sheath has a gooseneck construction so that a user may position it and the cable retains its shape. The fitting has a generally female form and a diameter suitable for gripping by a user and generally larger than the diameter of the cable itself. Opposite the fitting, the cable terminates in its tip 3 from which light emits. Effectively light and other radiation supplied into the fitting travels the length of the cable and emerges at the tip for illuminating a target selected by the user.

Figure 3A:
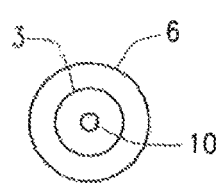
FIG. 3A provides an end view of the cable and FIG. 3B provides an opposite end view of the cable.
Figure 3B:
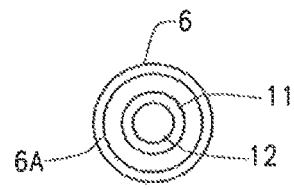

The user, and more particularly, the target, would view the end of the cable 2 shown in FIG. 3a. This end of the cable 2 operates as its tip 3 that a user generally and gently positions near an eye of a patient. The tip, along with the remainder of the invention, may have diagnostic applications and uses, therapeutic applications and uses, and both diagnostic and therapeutic applications and uses. The tip emits light through a distal aperture 10 of a slightly less diameter than that of the cable. The distal aperture has a transparent construction so that light of predetermined wavelengths emits from the tip and then travels on to the target location beneath the tip. Opposite the tip, the cable has its fitting 6 shown on end in FIG. 3b. The fitting has a round, hollow cylindrical shape, or female shape, and a diameter slightly more than that of the cable and a length that extends the fitting outwardly from the cable. The fitting length is at least half the diameter of the fitting and allows for a user to turn it for connection to the light source or radiation source. The fitting has a wall 6a that joins to a base 11 where the base is transverse to the cable. The base has a round shape and its own diameter. Centered in the base, a proximal aperture also has a transparent construction so that light of predetermined wavelengths enters the cable from the light source and for transmission over the length of the cable to the tip. Though the text so far has described light and other radiation traveling from base to tip through the cable, the Applicant foresees that the cable and related connections as transmitting light and other radiation just as well from tip through the cable back to the base. The invention can transmit radiation, including light, from either end to the other end, that is, from base to tip and from tip to base. This reflected light and other radiation then enters the generator 8 for other usage, as in triggering a detection device or other monitoring equipment whether stand alone or integrated with a microscope M.

Figure 4:
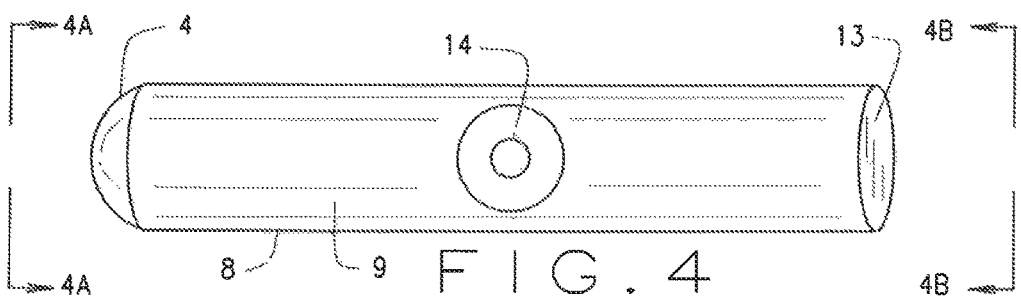
FIG. 4 provides a side view of the light generator of the invention.

Ahead of the cable 2, FIG. 4 shows the light generator 8 of a generally cylindrical form. The light generator has a case 9 of a round cylindrical shape and generally slender where its length exceeds that of its diameter noticeably, that is, by at least a factor of two. The case has a generally opaque construction so that light generated within it reaches the appropriate destination. The case 9 has two ends, the open end 4 that emanates light and an opposite closed end 13. The closed end has a position upon installation of away from the working end of an adjacent microscope. The closed end has an opaque construction and does not permit light to escape. Upon the case towards the closed end, the case has a male fitting 14 that receives the fitting 6 of the cable 2. The male fitting provides a firm connection to the fitting 6 and permits light to pass through the fitting and into the cable. The male fitting and fitting 6 cooperatively engage using mutual threading, a bayonet type lock, a snap on connection, a biased bearing, and the like. The male fitting has a location slightly away from the center of the case and at a single location as shown. Though a light generator is described, the Applicant foresees an alternate embodiment where the existing microscope provides light and supplies it to the cable 2 which connects directly to the surface of the microscope. This alternate embodiment would divert light from existing lamps in or upon a microscope into the cable 2.

Figure 4A:
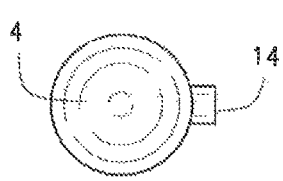
FIG. 4A provides an end view of the light generator and FIG. 4B provides an opposite end view of the light generator.
Figure 4B:
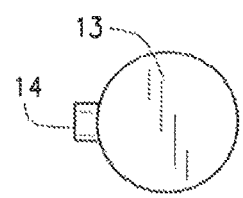
Figure 5:
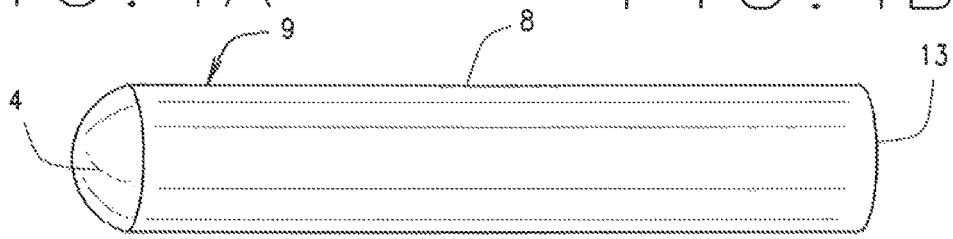
FIG. 5 shows a side view of the light generator opposite that of FIG. 4.

Turning the light generator, FIG. 4a shows the open end 4 in the foreground, such that light would exit the generator in this view. The male fitting 14 appears towards the right in this figure. Turning the light generator again, FIG. 4b shows the opposite end of the case with the closed end 13 in the foreground and no chance of light appearing from this end. Rotating the case about its length, FIG. 5 shows the case 9, its open end 4, and the closed end 13. The case appears smooth for the male fitting has turned into the plane of the figure, generally opposite that shown in FIG. 4.

In an alternate embodiment, the open end 4 has a light sensor located upon it. The light sensor determines the intensity of light incident upon it. That is, the light sensor detects light emitted from the cable to a target, usually upon an eye under treatment, and reflected back towards the light generator located upon a microscope M or other equipment. Reflected light previously emitted from the cable occurs when the open end has temporary closure as later described. The light sensor also detects the intensity of light adjacent to it. Adjacent light emitted from the open end occurs when the aperture to the cable has temporary closure also as later described.

Figure 6:
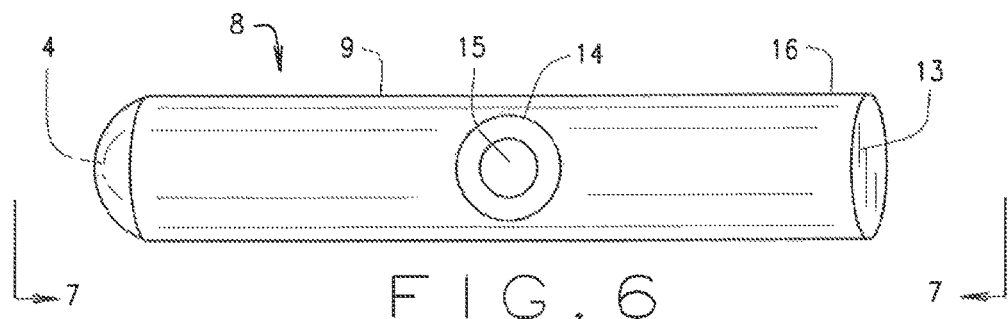
FIG. 6 shows a side view of the light generator.

Turning the light generator 8 so that its case 9 has the male fitting 14 forward again, FIG. 6 shows an enlarged view of the light generator. It has the case 9, open end 4, closed end 13, and male fitting 14 as before. Wiring, as at 16, approaches the case 9 and enters the case for delivery of electrical power and select controls. The male fitting also has its optical aperture 15 centered therein. The optical aperture admits light from within the generator through the male fitting and into a connecting cable. The optical aperture is at least transparent or alternatively has no physical form and is thus open completely to transmission of light through it.

Figure 7:
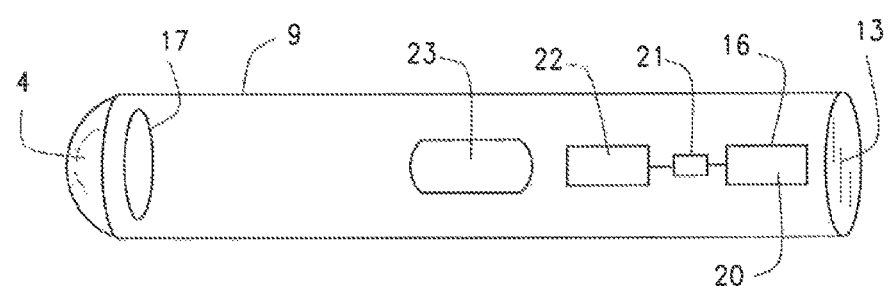
FIG. 7 shows a section view of the light generator.

FIG. 7 shows the internal components of the light generator 8 generally within the case 9. These components cooperate in the production, control, and transmission of light. The light typically has a wavelength of the visible spectrum though other wavelengths suitable for ophthalmic usage may emanate as desired. The wiring 16 enters the case 9 and connects to a power unit 20 that produces the electrical power of a voltage, amperage, and frequency desirable to create a selected light. The power unit then has electrical communication to a switch as at 21 that controls the electrical properties. The switch permits a user to at least turn the light generator on or off and alternatively to fine tune the electrical properties of the light generator 8. The switch then has electrical communication to a generator itself, as at 22. The generator receives the power with its properties from the switch and creates light of desired wavelength and intensity or alternatively radiation. The generator includes an incandescent bulb, a light emitting diode, a semiconductor laser, and the like. The generator then emits the light into the case towards the open end 4. The open end has a lens 17 before it that collects the light and then focuses it for emanation out the open end. The lens produces a beam of light with a focal point selected for the working distance of the user from the open end.

Though the preceding description refers to light emitted from the light generator, the Applicant foresees the generator emitting electromagnetic radiation selected from below the infrared range of the spectrum to above the ultraviolet range of the spectrum, including visible light. The generator may be operated upon a fixed wavelength of radiation or have the capability for adjusting the wavelength. The generator and related components of the invention will include shielding as needed for the radiation selected.

Though a light generator is described, the Applicant foresees the light generator as a multiplier laser. Such a laser would serve as a master laser creating light energy. The light from the master laser then divides upon individual fiber optic lines and each line then enters an examination room for attachment to a microscope or other equipment in the room.

Near the generator 22 and well before the lens 17, the light generator has a divider 23. The divider directs light either to the lens 17 then the open end 4 or alternatively into the male fitting 14 as previously shown. The divider allows a user to put all of the light into the cable or to use the open end at the election of the user. The divider effectively sends light along the case or serves as a shunt that moves light into the cable, or radiation transmitting member. The divider has at least two positions to accomplish its task, such as a first position permitting transmission of radiation, such as light, into the male fitting, and a second positing preventing that transmission.

Figures 8A, 8B, 8C, 8D:
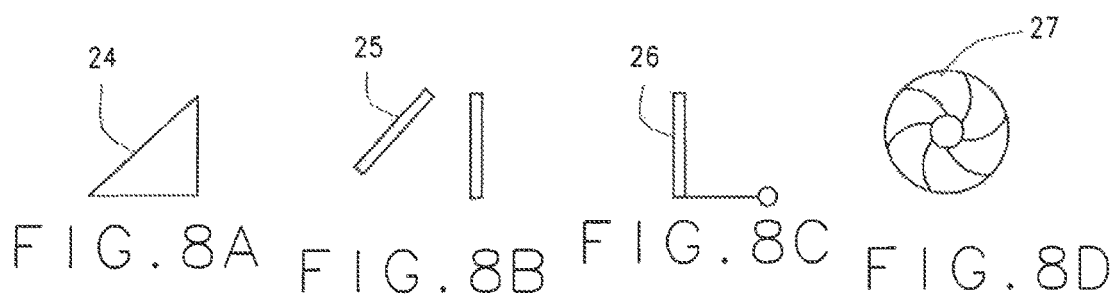
FIG. 8A describes a top view of the divider, FIG. 8*b* describes another top view of an alternate embodiment of the divider, FIG. 8*c* describes another top view of an alternate embodiment of the divider.
FIG. 8*d* shows a front view of an alternate embodiment of the divider; and, FIG. 9A illustrates a top sectional view of the divider in the closed position

The divider may take various forms as shown in FIGS. 8a through 8d. FIG. 8a shows a top view of a prism 24. The prism has two faces perpendicular to each other and spanned by a third face. Light through one face becomes incident on the third face and then reflects towards the other of the two faces, such as out to the male fitting. FIG. 8b shows a top view of a pair of mirrors 25. One mirror has a position transverse to the case 9 and the other mirror has a position at a forty five degree angle to the case. The other mirror's position allows for reflection of the light out to the male fitting. Alternatively, a mirror flip may be used, or a single mirror. FIG. 8c shows a top view of a shutter 26 with a right angle form and a pivot point on one end offset from the vertex. The shutter 26 pivots from an open position to a closed position, here shown, for the divider. In a further alternate embodiment, the divider has a multiple leaf concentric shutter as at 27 similar to that of a camera.

Figures 9A, 9B:
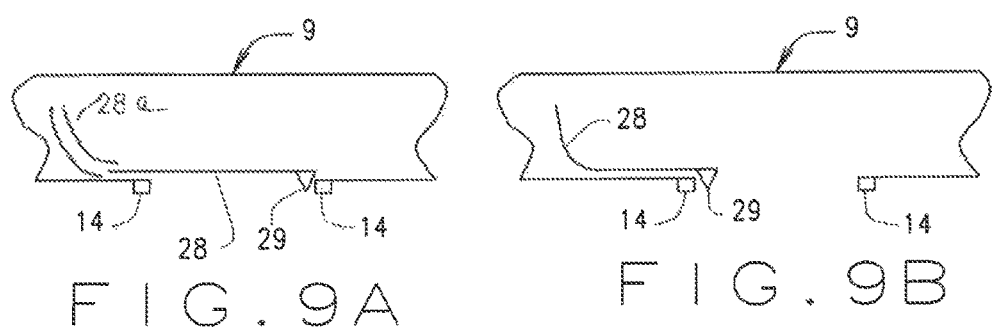
FIG. 9B illustrates a top section view of the divider in the open position.

And, FIG. 9a shows a partial top view of the case 9 with another alternate embodiment of the divider: an occluder 28. The occluder spans the optical aperture 15 inward from the male fitting 14 and it has two ends. The occluder has a tab 29 upon one end as shown towards one side of the male fitting. The tab extends outwardly from the occluder, that is, away from the center of the case. The occluder has a height and a length that cooperate to close the optical aperture, preventing passage of light. The occluder has an opaque construction but of a flexible material. The occluder appears away from its internal track as at 28a with the tab 29 furthest from the internal track. The internal track guides the occluder to curl into the case. FIG. 9b shows the occluder moved to an open position where light enters the optical aperture 15. To do so, a user presses the tab 29 and moves it towards the opposite side of the male fitting 14 from that shown in FIG. 9a. The occluder's construction then bends across the interior of the case and prevents light from reaching the open end 4, not shown. The occluder opens and closes the aperture, the optical aperture, of the male fitting.

From the aforementioned description, an endo-optic illuminator has been described. The endo-optic illuminator is uniquely capable of collocating a light source with diagnostic and treatment equipment, particularly for ophthalmic use though other medical and veterinary uses are foreseen. The endo-optic illuminator and its various components may be manufactured from many materials, including but not limited to, polymers, polyethylene, polypropylene, ferrous and non-ferrous metals, their alloys, and composites. The components may be of surgical grade and with anti-microbial characteristics.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

The preceding assembly steps and dimensional parameters remain as estimates by the Applicant calculated in coordination with accepted engineering and optics formulas using reasonable assumptions and appropriate simplifications. The Applicant asserts that the assembly steps and dimensional parameters have not approached finality but rather show that the assembly steps and dimensions of the invention may have a plausible adjustment given known engineering and optics principles. Actual assembly steps and dimensional parameters will remain within a range of the values provided here.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the specific details. In other instances, well known features are omitted or simplified in order not to obscure the illustrative embodiments.

Various operations have been described as multiple discrete operations, in a manner that is most helpful in understanding the present invention, however, the order of description should not be construed as to imply that these operations are necessarily order dependent. In particular, these operations need not be performed in the order of presentation.

Moreover, in the specification and the following claims, the terms "first," "second," "third" and the like are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to ascertain the nature of the technical disclosure. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

I claim:

1. An endo-optic illuminator, comprising:
   a radiation generator, said radiation generator is adapted to attach to a microscope, said radiation generator having an open end and an opposite closed end, a length, an optical aperture upon its length, a male fitting concentric with said optical aperture, wherein said open end transmits radiation, wherein said optical aperture transmits radiation, and wherein said closed end is opaque;
   a flexible, elongated, radiation transmitting member, said member having a length, two opposite ends, one end being a tip and an opposite end being a base, an opaque sheath upon the length of said member, wherein said member receives radiation into one of said ends and emits radiation from the other of said ends, said base having a fitting adapted to engage said male fitting; and,
   a divider within said radiation generator, said divider having optical communication into said fitting and into said optical aperture, said divider having a first position permitting transmission of radiation into said fitting and a second position preventing transmission of radiation into said fitting.

2. The endo-optic illuminator of claim 1 further comprising:
   said divider being one of a prism, at least one mirror, a pivoting shutter, an occluder, and a multiple leaf shutter.

3. The endo-optic illuminator of claim 2 further comprising:
   said occluder being generally flexible, having two ends with a tab upon one end.

4. The endo-optic illuminator of claim 2 wherein said radiation generator emits light, said radiation transmitting member transmits light, and said divider alters the path of light within said illuminator.

5. The endo-optic illuminator of claim 1 further comprising:
   said radiation generator having a power unit, a switch in electrical communication with said power unit, a generator in electrical communication with said switch and in communication with said divider, a lens proximate said open end, and a case containing said power unit, said switch, said generator, said divider, and said lens.

6. The endo-optic illuminator of claim 5 further comprising:
   said divider being one of a prism, at least one mirror, a pivoting shutter, an occluder, and a multiple leaf shutter.

7. The endo-optic illuminator of claim 6 further comprising:
   said case having an internal track outwardly from said male fitting, said occluder travelling within said internal track;
   said occluder being generally flexible, having two ends with a tab upon one end, said occluder having a first position within said internal track and said tab placing adjacent to one side of said male fitting wherein said first position exposes said optical aperture and a second position extended from said internal track across said male fitting and said tab placing adjacent to the opposite side of said male fitting wherein said second position closes said optical aperture.

8. The endo-optic illuminator of claim 5 wherein said radiation generator emits light and said radiation transmitting member transmits light.

9. The endo-optic illuminator of claim 1 wherein said radiation generator emits light and said radiation transmitting member transmits light.

10. The endo-optic illuminator of claim 1 wherein said radiation generator emits light, said radiation transmitting member transmits light, and said radiation transmitting member also receives light into said tip and emits light from said base.

11. An endo-optic illuminator, comprising:
    a radiation generator, said radiation generator is adapted to attach to a microscope, said radiation generator having an open end and an opposite closed end, a length, an optical aperture upon its length, a male fitting concentric with said optical aperture, wherein said open end transmits radiation, wherein said optical aperture transmits radiation, and wherein said closed end is opaque;
    a flexible, elongated, radiation transmitting member, said member having a length, two opposite ends, one end being a tip and an opposite end being a base, an opaque sheath upon the length of said member, wherein said member receives radiation into one of said ends and emits radiation from the other of said ends, said base having a fitting adapted to engage said male fitting; and,
    a divider within said radiation generator, said divider having optical communication into said fitting and into said optical aperture, said divider having a first position permitting transmission of radiation into said fitting and a second position preventing transmission of radiation into said fitting, said divider being one of a prism, at least one mirror, a pivoting shutter, an occluder, and a multiple leaf shutter; and,
    said radiation generator having a power unit, a switch in electrical communication with said power unit, a generator in electrical communication with said switch and in communication with said divider, a lens proximate said open end, a case containing said power unit, said switch, said generator, said divider, and said lens.

12. The endo-optic illuminator of claim 11 wherein said radiation generator emits light and said radiation transmitting member transmits light from said base through to said tip.

* * * * *